(12) United States Patent
LaRonde et al.

(10) Patent No.: US 8,357,385 B2
(45) Date of Patent: *Jan. 22, 2013

(54) COMBINATION THERAPY FOR THE TREATMENT OF BACTERIAL INFECTIONS

(75) Inventors: Frank LaRonde, Toronto (CA); Hanje Chen, Toronto (CA); Selva Sinnadurai, Scarborough (CA)

(73) Assignee: Interface Biologics Inc., Toronto (CA)

( * ) Notice: Subject to any disclaimer, the term of this patent is extended or adjusted under 35 U.S.C. 154(b) by 377 days.

This patent is subject to a terminal disclaimer.

(21) Appl. No.: 12/419,733

(22) Filed: Apr. 7, 2009

(65) Prior Publication Data

US 2010/0062974 A1  Mar. 11, 2010

Related U.S. Application Data

(60) Provisional application No. 61/123,231, filed on Apr. 7, 2008.

(51) Int. Cl.
*A61F 13/00* (2006.01)
*A61K 31/74* (2006.01)

(52) U.S. Cl. .................................... 424/422; 424/78.17

(58) Field of Classification Search .................. None
See application file for complete search history.

(56) References Cited

U.S. PATENT DOCUMENTS

| | | | |
|---|---|---|---|
| 2,631,146 A * | 3/1953 | Weidenheimer et al. | 540/345 |
| 6,432,389 B1 * | 8/2002 | Hansenne et al. | 424/59 |
| 2004/0039031 A1 * | 2/2004 | Cugnardey et al. | 514/354 |
| 2007/0020320 A1 * | 1/2007 | David et al. | 424/445 |
| 2010/0034862 A1 * | 2/2010 | Laronde et al. | 424/423 |

FOREIGN PATENT DOCUMENTS

| | | |
|---|---|---|
| CA | 2 243 649 | 8/1997 |
| CA | 2 417 389 | 2/2002 |
| CA | 2 438 346 | 3/2004 |
| CA | 2 539 868 | 4/2005 |
| CA | 2 467 321 | 11/2005 |
| CA | 2 611 577 | 9/2007 |

OTHER PUBLICATIONS

Bu et al. A Comparison of Topical Chlorhexidine, Ciprofloxacin, and Fortified Tobramycin/Cefazolin in Rabbit Models of *Staphylococcus* and *Pseudomonas* Keratitis. Journal of Ocular Pharmacology and Therapeutics, 1997.vol. 23, No. 3, pp. 213-220.*

Martin-Navarro et al. The potential pathogenicity of chlorhexidine-sensittive *Acanthamoeba* strains isolated from contact lens cases from asymptomatic individuals in Tenerife, Canary Islands, Spain. Journal of Medical Microbiology. 2008. vol. 57, pp. 1399-1404.*

Craig et al., *Modern Pharmacology*. $4^{th}$ Edition: 545-547, 555-557, 567, 569, 583-586, 651-654, and 849-851. (1994).

Jones et al., "Bacterial Resistance: A Worldwide Problem," *Diagn. Microbiol. Infect. Dis.* 31:379-388 (1998).

Murray,"Antibiotic Resistance," *Adv. Intern. Med.* 42:339-367 (1997).

Nakae, "Multiantibiotic Resistance Caused by Active Drug Extrusion in *Pseudomonas aeruginosa* and Other Gram-Negative Bacteria," *Microbiologia*. 13:273-284 (1997).

International Search Report (PCT/CA2009/000446), dated Jun. 8, 2009.

International Preliminary Report on Patentability and Written Opinion of the Searching Authority (PCT/CA2009/000446), dated Oct. 21, 2010.

* cited by examiner

*Primary Examiner* — Marcela M Cordero Garcia

(74) *Attorney, Agent, or Firm* — Clark & Elbing LLP; Kristina Bieker-Brady

(57) ABSTRACT

The invention features a method for treating a subject diagnosed with, or at risk of developing, a bacterial infection by administering to the subject a combination of biologically active agents.

6 Claims, No Drawings

US 8,357,385 B2

COMBINATION THERAPY FOR THE TREATMENT OF BACTERIAL INFECTIONS

CROSS-REFERENCE TO RELATED APPLICATIONS

This application claims benefit from U.S. Provisional Application No. 61/123,231, filed Apr. 7, 2008, hereby incorporated by reference.

BACKGROUND OF THE INVENTION

The present invention relates to the field of antibacterial therapy.

The use of antibiotics by humans can be seen as an evolutionary experiment of enormous magnitude, a window from which to view not-quite-natural selection operating in real time. Within 50 years, the number of species and strains of pathogenic and commensal bacteria resistant to antibiotics and the number of antibiotics to which they are resistant has increased virtually monotonically world-wide. As a result, infections that had been readily treatable by chemotherapy may no longer be so. It is clear that the evolution and spread of resistance can be attributed to the use and overuse of antibiotics. Increased resistance of bacterial infections to antibiotic treatment has been extensively documented and has now become a generally recognized medical problem, particularly with nosocomial infections. See, for example, Jones et al., *Diagn. Microbiol. Infect. Dis.* 31:379-388, 1998; Murray, *Adv. Intern. Med.* 42:339-367, 1997; and Nakae, *Microbiologia* 13:273-284, 1997.

Throughout the developed world there is public and governmental concern about the increasing prevalence of antimicrobial resistance to chemotherapy in bacteria that cause diseases in humans. Many pathogens exist for which there are few effective treatments, and the number of strains resistant to available drugs is continually increasing. New antimicrobial agents and improved methods are thus needed for the treatment and prevention of infections by such pathogens.

SUMMARY OF THE INVENTION

We have discovered that a combination of a membrane active biocide (e.g., chlorhexidine) and a second agent selected from fluoroquinolones, aminoglycosides, β-lactams, glycopeptide antibiotics, sulfonamides, and antifungal azoles is more effective in treating bacterial infections and reducing bacterial growth than either agent alone. We have also discovered that a combination of a sulfonamide (e.g., sulfamethoxazole) and a second agent selected from β-lactams and antifungal azoles is more effective in treating bacterial infections and reducing bacterial growth than either agent alone. Thus, the invention features compositions, methods, and kits including these effective combinations, which can be useful for the treatment and prevention of infections.

Accordingly, in a first aspect the invention features a composition including a membrane active biocide and a second agent selected from fluoroquinolones, aminoglycosides, β-lactams, glycopeptide antibiotics, sulfonamides, and antifungal azoles in amounts that together are sufficient in vivo to treat a bacterial infection.

In a related aspect, the invention features a biodegradable polymer including a first repeating unit and a second repeating unit, the first repeating unit including a membrane active biocide and the second repeating unit including a second agent selected from fluoroquinolones, aminoglycosides, β-lactams, glycopeptide antibiotics, sulfonamides, and antifungal azoles.

The invention further features a composition including a biodegradable polymer having a first repeating unit and a second repeating unit, the first repeating unit including a membrane active biocide and the second repeating unit including a second agent selected from fluoroquinolones, aminoglycosides, β-lactams, glycopeptide antibiotics, sulfonamides, and antifungal azoles.

The invention also features a composition including (i) a biodegradable polymer including a repeating unit including a membrane active biocide and (ii) a second agent selected from fluoroquinolones, aminoglycosides, β-lactams, glycopeptide antibiotics, sulfonamides, and antifungal azoles.

In a related aspect the invention features a composition including (i) a biodegradable polymer including a repeating unit including a second agent selected from fluoroquinolones, aminoglycosides, β-lactams, glycopeptide antibiotics, sulfonamides, and antifungal azoles and (ii) a membrane active biocide.

The invention further features a composition including (i) a first biodegradable polymer including a repeating unit including a membrane active biocide and (ii) a second biodegradable polymer including a repeating unit including a second agent selected from fluoroquinolones, aminoglycosides, β-lactams, glycopeptide antibiotics, sulfonamides, and antifungal azoles.

The invention further features a method of reducing bacterial growth on a surface by contacting the surface with a composition including a membrane active biocide and a second agent selected from fluoroquinolones, aminoglycosides, β-lactams, glycopeptide antibiotics, sulfonamides, and antifungal azoles in amounts that together are effective to reduce bacterial growth.

The invention also features a method of reducing bacterial growth on a surface by coating the surface with a biodegradable polymer including a first repeating unit and a second repeating unit, the first repeating unit including a membrane active biocide and the second repeating unit including a second agent selected from fluoroquinolones, aminoglycosides, β-lactams, glycopeptide antibiotics, sulfonamides, and antifungal azoles.

The invention further features a method of reducing fungal growth on a surface by contacting the surface with a composition including a membrane active biocide and a second agent selected from fluoroquinolones, aminoglycosides, β-lactams, glycopeptide antibiotics, sulfonamides, and antifungal azoles in amounts that together are effective to reduce fungal growth.

The invention also features a method of reducing fungal growth on a surface by coating the surface with a biodegradable polymer including a first repeating unit and a second repeating unit, the first repeating unit including a membrane active biocide and the second repeating unit including a second agent selected from fluoroquinolones, aminoglycosides, β-lactams, glycopeptide antibiotics, sulfonamides, and antifungal azoles.

In certain embodiments of the above methods, the surface is, for example, a surface of an implantable medical device (e.g., a cardiac-assist device, a catheter, a stent, a prosthetic implant, a suture, a cuff, a mesh, a hernia patch, a wound dressing, a bandage, an artificial sphincter, or a drug delivery device) or any other surface described herein.

The invention also features a method of treating a bacterial infection in a subject, the method including administering a membrane active biocide and a second agent selected from fluoroquinolones, aminoglycosides, β-lactams, glycopeptide antibiotics, sulfonamides, and antifungal azoles to the subject in amounts that together are sufficient in vivo to treat the bacterial infection.

The invention also features a method of treating a fungal infection in a subject, the method including administering a membrane active biocide and a second agent selected from fluoroquinolones, aminoglycosides, β-lactams, glycopeptide antibiotics, sulfonamides, and antifungal azoles to the subject in amounts that together are sufficient in vivo to treat the fungal infection.

In certain embodiments, the membrane active biocide and the second agent are administered for prophylaxis against an infection resulting from a surgical procedure or implantation of a medical device (e.g., a cardiac-assist device, a catheter, a stent, a prosthetic implant, a suture, a cuff, a mesh, a hernia patch, a wound dressing, a bandage, an artificial sphincter, a drug delivery device, or any other medical device described herein).

In still other embodiments, the method of treating includes contacting the subject with a biodegradable polymer including a first repeating unit and a second repeating unit, the first repeating unit including a membrane active biocide and the second repeating unit including a second agent selected from fluoroquinolones, aminoglycosides, β-lactams, glycopeptide antibiotics, sulfonamides, and antifungal azoles.

In certain embodiments, the method of treating includes contacting the subject with (i) a biodegradable polymer including a repeating unit including a membrane active biocide and (ii) and a second agent selected from fluoroquinolones, aminoglycosides, β-lactams, glycopeptide antibiotics, sulfonamides, and antifungal azoles. Alternatively, the method of treating includes contacting the subject with (i) a biodegradable polymer including a repeating unit including a second agent selected from fluoroquinolones, aminoglycosides, β-lactams, glycopeptide antibiotics, sulfonamides, and antifungal azoles and (ii) a membrane active biocide.

In still other embodiments, the method of treating includes contacting the subject with (i) a first biodegradable polymer including a repeating unit including a membrane active biocide and (ii) a second biodegradable polymer including a repeating unit including a second agent selected from fluoroquinolones, aminoglycosides, β-lactams, glycopeptide antibiotics, sulfonamides, and antifungal azoles.

The invention features a kit including: (i) a composition including a membrane active biocide and a second agent selected from fluoroquinolones, aminoglycosides, β-lactams, glycopeptide antibiotics, sulfonamides, and antifungal azoles; and (ii) instructions for administering the composition to a subject diagnosed with or at risk of developing a bacterial infection.

The invention further features a kit including: (i) a membrane active biocide; (ii) a second agent selected from fluoroquinolones, aminoglycosides, β-lactams, glycopeptide antibiotics, sulfonamides, and antifungal azoles; and (iii) instructions for administering the membrane active biocide and the fluoroquinolone to a subject diagnosed with or at risk of developing a bacterial infection.

The invention also features a kit including: (i) an implantable medical device; (ii) a composition including a membrane active biocide and a second agent selected from fluoroquinolones, aminoglycosides, β-lactams, glycopeptide antibiotics, sulfonamides, and antifungal azoles; and (iii) instructions for coating the implantable medical device with the composition.

In certain embodiments of the kits of the invention, the composition is a biodegradable polymer including a first repeating unit and a second repeating unit, the first repeating unit including a membrane active biocide and the second repeating unit including the second agent. Alternatively, the composition is a mixture of (i) a biodegradable polymer including a repeating unit including a membrane active biocide and (ii) the second agent; a mixture of (i) a biodegradable polymer including a repeating unit including the second agent and (ii) a membrane active biocide; or a mixture of (i) a first biodegradable polymer including a repeating unit including a membrane active biocide and (ii) the second biodegradable polymer including a repeating unit including the second agent.

In still another related aspect, the invention features a composition including a sulfonamide and a second agent selected from β-lactams and antifungal azoles in amounts that together are sufficient in vivo to treat a bacterial infection.

In a related aspect, the invention features a biodegradable polymer including a first repeating unit and a second repeating unit, the first repeating unit including a sulfonamide and the second repeating unit including a second agent selected from β-lactams and antifungal azoles.

The invention further features a composition including a biodegradable polymer having a first repeating unit and a second repeating unit, the first repeating unit including a sulfonamide and the second repeating unit including a second agent selected from β-lactams and antifungal azoles.

The invention also features a composition including (i) a biodegradable polymer including a repeating unit including a sulfonamide and (ii) a second agent selected from β-lactams and antifungal azoles.

In a related aspect the invention features a composition including (i) a biodegradable polymer including a repeating unit including a second agent selected from β-lactams and antifungal azoles and (ii) a sulfonamide.

The invention further features a composition including (i) a first biodegradable polymer including a repeating unit including a sulfonamide and (ii) a second biodegradable polymer including a repeating unit including a second agent selected from β-lactams and antifungal azoles.

The invention further features a method of reducing bacterial growth on a surface by contacting the surface with a composition including a sulfonamide and a second agent selected from β-lactams and antifungal azoles in amounts that together are effective to reduce bacterial growth.

The invention also features a method of reducing bacterial growth on a surface by coating the surface with a biodegradable polymer including a first repeating unit and a second repeating unit, the first repeating unit including a sulfonamide and the second repeating unit including a second agent selected from β-lactams and antifungal azoles.

The invention further features a method of reducing fungal growth on a surface by contacting the surface with a composition including a sulfonamide and a second agent selected from β-lactams and antifungal azoles in amounts that together are effective to reduce fungal growth.

The invention also features a method of reducing fungal growth on a surface by coating the surface with a biodegradable polymer including a first repeating unit and a second repeating unit, the first repeating unit including a sulfonamide and the second repeating unit including a second agent selected from β-lactams and antifungal azoles.

In certain embodiments of the above methods, the surface is, for example, a surface of an implantable medical device (e.g., a cardiac-assist device, a catheter, a stent, a prosthetic implant, a suture, a cuff, a mesh, a hernia patch, a wound dressing, a bandage, an artificial sphincter, or a drug delivery device) or any other surface described herein.

The invention also features a method of treating a bacterial infection in a subject, the method including administering a sulfonamide and a second agent selected from β-lactams and antifungal azoles to the subject in amounts that together are sufficient in vivo to treat the bacterial infection.

The invention also features a method of treating a fungal infection in a subject, the method including administering a sulfonamide and a second agent selected from β-lactams and antifungal azoles to the subject in amounts that together are sufficient in vivo to treat the fungal infection.

In certain embodiments, the sulfonamide and the second agent are administered for prophylaxis against an infection resulting from a surgical procedure or implantation of a medical device (e.g., a cardiac-assist device, a catheter, a stent, a prosthetic implant, a suture, a cuff, a mesh, a hernia patch, a wound dressing, a bandage, an artificial sphincter, a drug delivery device, or any other medical device described herein).

In still other embodiments, the method of treating includes contacting the subject with a biodegradable polymer including a first repeating unit and a second repeating unit, the first repeating unit including a sulfonamide and the second repeating unit including a second agent selected from β-lactams and antifungal azoles.

In certain embodiments, the method of treating includes contacting the subject with (i) a biodegradable polymer including a repeating unit including a sulfonamide and (ii) and a second agent selected from β-lactams and antifungal azoles. Alternatively, the method of treating includes contacting the subject with (i) a biodegradable polymer including a repeating unit including a second agent selected from β-lactams and antifungal azoles and (ii) a sulfonamide.

In still other embodiments, the method of treating includes contacting the subject with (i) a first biodegradable polymer including a repeating unit including a sulfonamide and (ii) a second biodegradable polymer including a repeating unit including a second agent selected from β-lactams and antifungal azoles.

The invention features a kit including: (i) a composition including a sulfonamide and a second agent selected from β-lactams and antifungal azoles; and (ii) instructions for administering the composition to a subject diagnosed with or at risk of developing a bacterial infection.

The invention further features a kit including: (i) a sulfonamide; (ii) a second agent selected from β-lactams and antifungal azoles; and (iii) instructions for administering the sulfonamide and the fluoroquinolone to a subject diagnosed with or at risk of developing a bacterial infection.

The invention also features a kit including: (i) an implantable medical device; (ii) a composition including a sulfonamide and a second agent selected from β-lactams and antifungal azoles; and (iii) instructions for coating the implantable medical device with the composition.

In certain embodiments of the kits of the invention, the composition is a biodegradable polymer including a first repeating unit and a second repeating unit, the first repeating unit including a sulfonamide and the second repeating unit including the second agent. Alternatively, the composition is a mixture of (i) a biodegradable polymer including a repeating unit including a sulfonamide and (ii) the second agent; a mixture of (i) a biodegradable polymer including a repeating unit including the second agent and (ii) a sulfonamide; or a mixture of (i) a first biodegradable polymer including a repeating unit including a sulfonamide and (ii) the second biodegradable polymer including a repeating unit including the second agent.

Bacterial and fungal infections that can be treated using the methods of the invention include, without limitation, group consisting of a community-acquired pneumonia, upper and lower respiratory tract infection, skin and soft tissue infection, bone and joint infection, hospital-acquired lung infection, acute bacterial otitis media, bacterial pneumonia, complicated infection, noncomplicated infection, pyelonephritis, intra-abdominal infection, deep-seated abcess, bacterial sepsis, central nervous system infection, bacteremia, wound infection, peritonitis, meningitis, infections after burn, urogenital tract infection, gastro-intestinal tract infection, pelvic inflammatory disease, endocarditis, intravascular infection, and any other bacterial infections described herein. The infections to be treated may be caused by Gram-positive bacteria. These include, without limitation, infections by, *Staphylococcus aureus, Staphylococcus epidermidis, Enterococcus faecalis, Enterococcus faecium, Clostridium perfringens, Clostridium difficile, Streptococcus pyogenes, Streptococcus pneumoniae*, other *Streptococcus* spp., and other *Clostridium* spp. More specifically, the infections may be caused by a Gram-positive coccus, or by a drug-resistant Gram-positive coccus. Exemplary Gram-positive cocci are, without limitation, *S. aureus, S. epidermidis, S. pneumoniae, S. pyogenes, M. catarrhalis, C. difficile, H. pylori, Chlamydia* spp., and *Enterococcus* spp. Furthermore, the methods and compositions described herein are useful for treating an infection by multi-drug resistant bacteria. Resistant strains of bacteria include penicillin-resistant, methicillin-resistant, quinolone-resistant, macrolide-resistant, and/or vancomycin-resistant bacterial strains. The multi-drug resistant bacterial infections to be treated using the methods of the invention include, for example, infections by penicillin-, methicillin-, macrolide-, vancomycin-, and/or quinolone-resistant *Streptococcus pneumoniae*; penicillin-, methicillin-, macrolide-, vancomycin-, and/or quinolone-resistant *Staphylococcus aureus*; penicillin-, methicillin-, macrolide-, vancomycin-, and/or quinolone-resistant *Streptococcus pyogenes*; and penicillin-, methicillin-, macrolide-, vancomycin-, and/or quinolone-resistant *enterococci*. The infections to be treated may be caused by Gram-negative bacteria. The infections to be treated may be fungal infections caused by *Candida* spp.

The invention further features a shaped article including a composition of the invention.

In a related aspect, the invention features a shaped article including a biodegradable polymer of the invention.

Shaped articles of the invention can be in the form of an implantable medical device (e.g., a cardiac-assist device, a catheter, a stent, a prosthetic implant, a suture, a cuff, a mesh, a hernia patch, a wound dressing, a bandage, an artificial sphincter, or a drug delivery device), self-supporting film, fiber, or any other shaped article described herein.

In the methods, kits, compositions, and biodegradable polymers of the invention, the membrane active biocide can be selected from chlorhexidine, polymyxin B-nonapeptide, bacitracin, aztreonam, benzalkonium salts, metal chelators, and any other membrane active biocide described herein. In certain embodiments, the membrane active biocide is chlorhexidine.

In the methods, kits, compositions, and biodegradable polymers of the invention, the fluoroquinolone can be selected from ciprofloxacin, enrofloxacin, enoxacin, gatifloxacin, gemifloxacin, levofloxacin, lomefloxacin, moxifloxacin, norfloxacin, ofloxacin, sparfloxacin, trovafloxacin, difloxacin, cinofloxacin, pefloxacin, tosufloxacin, temafloxacin, fleroxacin, amifloxacin, binfloxacin, danofloxacin, marbofloxacin, ruflocaxin, sarafloxacin, and any other fluoroquinolone described herein. In certain embodiments, the fluoroquinolone is ciprofloxacin.

In the methods, kits, compositions, and biodegradable polymers of the invention, the aminoglycoside can be selected from amikacin, apramycin, arbekacin, bambermycins, butirosin, dibekacin, dihydrostreptomycin, fortimicin(s), fradiomycin, gentamicin, ispamicin, kanamycin, micronomicin, neomycin, neomycin undecylenate, netilmicin, paromomycin, ribostamycin, sisomicin, spectinomycin, streptomycin, streptonicozid, and tobramycin. In certain embodiments, the aminoglycoside is gentamicin.

In the methods, kits, compositions, and biodegradable polymers of the invention, the β-lactam can be selected from amidinocillin, amdinocillin, pivoxil, amoxicillin, ampicillin, aspoxicillin, azidocillin, azlocillin, bacampicillin, benzylpenicillinic acid, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzhydrylamine, penicillin G calcium, penicillin G hydragamine, penicillin G potassium, penicillin G, procaine, penicillin N, penicillin O, penicillin V, penicillin V benzathine, penicillin V hydrabamine, penimepicycline, phenethicillin, piperacillin, pivapicillin, propicillin, quinacillin, sulbenicillin, talampicillin, temocillin and ticarcillin. In certain embodiments, the β-lactam is amoxicillin.

In the methods, kits, compositions, and biodegradable polymers of the invention, the glycopeptide antibiotic can be selected from actaplanin, actinoidin, ardacin, avoparcin, azureomycin, balhimycin, chloroorientiein, chloropolysporin, decaplanin, N-demethylvancomycin, eremomycin, galacardin, helvecardin, izupeptin, kibdelin, orenticin, parvodicin, ramoplanin, ristocetin, ristomycin, synmonicin, teicoplanin, vancomycin, and vancomycin B. In certain embodiments, the glycopeptide antibiotic is vancomycin.

In the methods, kits, compositions, and biodegradable polymers of the invention, the sulfonamide can be selected from acetyl sulfamethoxypyrazine, acetyl sulfisoxazole, azosulfamide, benzylsulfamide, chloramine-β, chloramine-T, dichloramine-T, formosulfathiazole, N2-formyl-sulfisomidine, N4-β-D-glucosylsulfanilamide, mafenide, 4'-(methylsulfamoyl)sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicyclic acid, N4-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine and sulfisoxazole. In certain embodiments, the sulfonamide is sulfamethoxazole.

In the methods, kits, compositions, and biodegradable polymers of the invention, the antifungal azole can be selected from miconazole, ketoconazole, clotrimazole, fluconazole, voriconazole, ravuconazole, azaconazole, bromuconazole bitertanol, propiconazole, difenoconazole, diniconazole, cyproconazole, epoxiconazole, fluquinconazole, flusilazole, flutriafol, hexaconazole, itraconazole, imazalil, imibenconazole, ipconazole, tebuconazole, tetraconazole, fenbuconazole, metconazole, myclobutanil, perfurazoate, penconazole, posaconazole, pyrifenox, prochloraz, terconazole, triadimefon, triadimenol, triflumizole, and triticonazole. In certain embodiments, the antifungal azole is miconazole.

As used herein, the term "aminoglycosides" refers to a class of antibiotics derived at least part from a saccharide or polysaccharide and having the empirical formula $C_m H_n N_p O_q$ (where m, n, p, and q are appropriate integers). For instance, the aminoglycosides are oligosaccharides consisting of an aminocyclohexanol moiety glycosidically linked to other amino sugars. Streptomycin, one of the best studied of the group, is produced by *Streptomyces griseus*. Streptomycin, and many other aminoglycosides, inhibits protein synthesis in the target organisms. Aminoglycosides include, without limitation, amikacin, apramycin, arbekacin, bambermycins, butirosin, dibekacin, dihydrostreptomycin, fortimicin(s), fradiomycin, gentamicin, ispamicin, kanamycin, micronomicin, neomycin, neomycin undecylenate, netilmicin, paromomycin, ribostamycin, sisomicin, spectinomycin, streptomycin, streptonicozid, and tobramycin. In certain embodiments, the aminoglycoside is gentamicin.

By "an amount sufficient" is meant the amount of a compound, a combination of compounds, or a biodegradable polymer used in the methods, compositions, and/or kits of the invention, required to treat or prevent a bacterial or fungal infection in a clinically relevant manner. A sufficient amount of a compound, a combination of compounds, or a biodegradable polymer used to practice the present invention for therapeutic treatment of conditions caused by or contributing to a bacterial or fungal infection can vary depending upon the manner of administration, the age, body weight, and general health of the subject. Ultimately, the prescribers will decide the appropriate amount and dosage regimen.

As used herein, the term "antifungal azoles" refers to any member of the class of anti-fungal compounds having a five-membered ring of three carbon atoms and two nitrogen atoms (imidazoles) or two carbon atoms and three nitrogen atoms (triazoles). Antifungal azoles include, without limitation, miconazole, ketoconazole, clotrimazole, fluconazole, voriconazole, ravuconazole, azaconazole, bromuconazole bitertanol, propiconazole, difenoconazole, diniconazole, cyproconazole, epoxiconazole, fluquinconazole, flusilazole, flutriafol, hexaconazole, itraconazole, imazalil, imibenconazole, ipconazole, tebuconazole, tetraconazole, fenbuconazole, metconazole, myclobutanil, perfurazoate, penconazole, posaconazole, pyrifenox, prochloraz, terconazole, triadimefon, triadimenol, triflumizole, and triticonazole.

By "bacterial infection" is meant the invasion of a host by pathogenic bacteria. For example, the infection may include the excessive growth of bacteria that are normally present in or on the body of a subject (i.e., an animal or human subject) or growth of bacteria that are not normally present in or on a subject. More generally, a bacterial infection can be any situation in which the presence of a bacterial population(s) is damaging to a host body. Thus, a subject is "suffering" from a bacterial infection when an excessive amount of a bacterial population is present in or on the person's body, or when the presence of a bacterial population(s) is damaging the cells or other tissue of the person.

As used herein, the term "β-lactams" refers to a class of antibiotics which a beta-lactam ring (a four-member heteroatomic ring structure including three carbon atoms and one nitrogen atom and linked as a cyclic amide). β-lactams include, without limitation, amidinocillin, amdinocillin, pivoxil, amoxicillin, ampicillin, aspoxicillin, azidocillin, azlocillin, bacampicillin, benzylpenicillinic acid, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzhydrylamine, penicillin G calcium, penicillin G hydragamine, penicillin G potassium, penicillin G, procaine, penicillin N, penicillin O, penicillin V, penicillin V benzathine, penicillin V hydrabamine, penimepicycline, phenethicillin, piperacillin, pivapicillin, propicillin, quinacillin, sulbenicillin, talampicillin, temocillin and ticarcillin.

By "effective" amount is meant the amount of a compound, a combination of compounds, or a biodegradable polymer used in the methods, compositions, and/or kits of the invention, required to reduce bacterial or fungal growth on a surface in comparison to the bacterial or fungal growth observed for the same surface under the same conditions, but in the absence of a compound, a combination of compounds, or a biodegradable polymer of the invention. Such amount is referred to as an "effective" amount.

As used herein, the term "fluoroquinolones" refers to a class of antibiotics which exert their antibacterial effects by inhibiting bacterial DNA gyrase and which include a fluorinated quinolone ring system. Fluoroquinolones which can be used in the devices, compositions, and methods of the invention include, without limitation, those described in patent publications BE870576; DE3142854; EP047005; EP206283; BE887574; EP221463; EP140116; EP131839; EP154780; EP078362; EP310849; EP520240; and U.S. Pat. Nos. 4,448,962; 4,499,091; 4,704,459; 4,795,751; 4,668,784; and 5,532,239, each of which is incorporated herein by reference. Exemplary fluoroquinolones which can be used in the devices, compositions, and methods of the invention include, without limitation, ciprofloxacin (commercially available as Cipro®), enrofloxacin (commercially available as Baytril®), enoxacin (commercially available as Penetrex®), gatifloxacin (commercially available as Tequin®), gemifloxacin (commercially available as Factive®), levofloxacin (commercially available as Levaquin®), lomefloxacin (commercially available as Maxaquin®), moxifloxacin (commercially available as Avelox®), norfloxacin (commercially available as Noroxin®), ofloxacin (commercially available as Floxin®), sparfloxacin (commercially available as Zagam®), trovafloxacin (commercially available as Trovan®), difloxacin, cinofloxacin, pefloxacin, tosufloxacin, temafloxacin, fleroxacin, amifloxacin, binfloxacin, danofloxacin, marbofloxacin, ruflocaxin, and sarafloxacin.

By "fungal infection" is meant the invasion of a host by pathogenic fungi. For example, the infection may include the excessive growth of fungi that are normally present in or on the body of a subject (i.e., an animal or human subject) or growth of fungi that are not normally present in or on a subject. More generally, a fungal infection can be any situation in which the presence of a fungal population(s) is damaging to a host body. Thus, a subject is "suffering" from a fungal infection when an excessive amount of a fungal population is present in or on the person's body, or when the presence of a fungal population(s) is damaging the cells or other tissue of the person.

As used herein, the term "glycopeptide antibiotics" refers to a class of antibiotics which are oligopeptide (e.g., heptapeptide) antibiotics, characterized by a ring peptide core and optionally substituted with saccharide groups, such as vancomycin or vancomycin-B. Glycopeptide antibiotics include, without limitation, A477, A35512, A40926, A41030, A42867, A47934, A80407, A82846, A83850, A84575, AB-65, actaplanin, actinoidin, ardacin, avoparcin, azureomycin, balhimycin, chloroorientiein, chloropolysporin, decaplanin, N-demethylvancomycin, eremomycin, galacardin, helvecardin, izupeptin, kibdelin, LL-AM374, mannopeptin, MM45289, MM47756, MM47761, MM49721, MM47766, MM55260, MM55266, MM55270, MM56597, MM56598, OA-7653, orenticin, parvodicin, ramoplanin, ristocetin, ristomycin, synmonicin, teicoplanin, UK-68597, UK-69542, UK-72051, vancomycin, and vancomycin B (see, e.g., "Glycopeptides Classification, Occurrence, and Discovery," by Rao R C and Crandall L W, in Drugs and the Pharmaceutical Sciences, Volume 63, Ramakrishnan N (ed.), Marcal Dekker, Inc., the entire disclosure of which is herein incorporated by reference). Glycopeptide antibiotics also include the general class of glycopeptides disclosed above in their aglycone form.

As used herein, the term "membrane active biocide" refers to a biocidal membrane permeabilizer. Membrane active biocides include, without limitation, cationic biguanide antibacterial agents (e.g., chlorhexidine), polymyxin B-nonapeptide, bacitracin, aztreonam, quaternary ammonium compounds (e.g., benzalkonium salts), and metal chelators, such as ethylenediaminetetraacetate (EDTA).

As used herein, the term "sulfonamides" refers to a class of antibiotics which include a sulfonamide group. Sulfonamides include, without limitation, acetyl sulfamethoxypyrazine, acetyl sulfisoxazole, azosulfamide, benzylsulfamide, chloramine-β, chloramine-T, dichloramine-T, formosulfathiazole, N2-formyl-sulfisomidine, N4-β-D-glucosylsulfanilamide, mafenide, 4'-(methyl-sulfamoyl)sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicyclic acid, N4-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine and sulfisoxazole.

As used herein, the term "treating" refers to administering a pharmaceutical composition, or a biodegradable polymer of the invention, for prophylactic and/or therapeutic purposes. A "prophylactic" use refers to reducing the likelihood or severity of a condition or disease in a subject who is not yet ill, but who is susceptible to, or otherwise at risk of, a particular disease by administering treatment to the subject. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

By "subject" is meant any animal (e.g., a human). Other animals that can be treated using the methods, compositions, and kits of the invention include horses, dogs, cats, pigs, goats, rabbits, hamsters, monkeys, guinea pigs, rats, mice, lizards, snakes, sheep, cattle, fish, and birds.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Desirably, the pharmaceutical salt is a zinc salt.

Other features and advantages of the invention will be apparent from the Detailed Description and the claims.

DETAILED DESCRIPTION

We have discovered that a combination of a membrane active biocide (e.g., chlorhexidine) and a second agent selected from fluoroquinolones, aminoglycosides, β-lactams, glycopeptide antibiotics, sulfonamides, and antifungal azoles is more effective in treating bacterial infections and reducing bacterial growth than either agent alone. We have also discovered that a combination of a sulfonamide (e.g., sulfamethoxazole) and a second agent selected from β-lactams and antifungal azoles is more effective in treating bacterial infections and reducing bacterial growth than either agent alone. Thus, the invention features compositions, methods, and kits including these effective combinations, which can be useful for the treatment and prevention of infections.

The invention is described in greater detail below.

Therapy

The compositions, methods, and kits described herein can be used to treat or prevent bacterial and/or fungal infections as well as diseases associated with bacterial and/or fungal infections.

Bacterial infections that can be treated or prevented using the combinations of the invention include, for example, respiratory tract infections (e.g., inhalation anthrax), acute bacterial otitis media, bacterial pneumonia, urinary tract infections, complicated infections, noncomplicated infections, pyelonephritis, intra-abdominal infections, deep-seated abcesses, bacterial sepsis, skin and skin structure infections (e.g., cutaneous anthrax), soft tissue infections (e.g., endometritis), bone and joint infections (e.g., osteomyelitis, septic arthritis), central nervous system infections (e.g., meningitis), bacteremia, wound infections, peritonitis, meningitis, infections after burn, urogenital tract infections, gastrointestinal tract infections (e.g., antibiotic-associated colitis, gastrointestinal anthrax), pelvic inflammatory disease, and endocarditis.

Fungal infections that can be treated or prevented using the combinations of the invention include, for example, superficial or systemic mycoses. Superficial mycoses include tinea capitis, tinea corporis, tinea pedis, onychomycosis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis, paracoccidioidomycosis, North American blastomycosis, histoplasmosis, coccidioidomycosis, and sporotrichosis.

Other Uses

Combinations of the invention can be incorporated into, for example, unpreserved food, beverages, contact lens products, food ingredients, or cosmetics, such as lotions, creams, gels, ointments, soaps, shampoos, conditioners, antiperspirants, deodorants, mouthwash, contact lens products, enzyme formulations, in an amount effective for killing or inhibiting the growth of fungal or bacterial pathogens.

Thus, a combination of the invention may be useful as a disinfectant, e.g., in the treatment of acne, eye infections, mouth infections, fingernail infections, top nail infections, skin infections, wounds, or in treating infections caused by the insertion of stents. Combinations of the invention are also useful for cleaning, disinfecting, or inhibiting fungal or bacterial growth on any hard surface. Examples of surfaces which may advantageously be contacted with a combination of the invention are surfaces of process equipment used in dairies, chemical or pharmaceutical process plants, water sanitation systems, paper pulp processing plants, water treatment plants, cooling towers, cooking utensils, or surfaces in any area in which food is prepared (e.g., hospitals, nursing homes, or restaurants).

In addition, combinations of the invention are useful for cleaning, disinfecting, or inhibiting fungal or bacterial growth on or in an in-dwelling device in a patient. In-dwelling devices include, but are not limited to, surgical and dental implants, prosthetic devices, artificial joints, heart valves, pacemakers, vascular grafts, vascular catheters, stents, cerebrospinal fluid shunts, urinary catheters, and continuous ambulatory peritoneal dialysis (CAPD) catheters. A combination of the invention may be used to bathe an in-dwelling device immediately before insertion. Alternatively, the combination may be administered by injection to achieve a local or systemic effect against relevant micro-organisms shortly before insertion of an in-dwelling device. Treatment may be continued after surgery during the in body time of the device.

Moreover, the compositions of the invention are useful as veterinary products for treating socially and/or economically valuable non-human vertebrate animals, such as pets and laboratory animals (horses, dogs, cats, rabbits, hamsters, monkeys, guinea pigs, rats, mice, lizards, snakes), livestock, fish, captive aquatic mammals, and birds. For land based animals, the compositions can be incorporated into feed, drinking water, or administered by IV, topically, or by other methods suitable for treating the particular animal in need of such treatment. For fish and other aquatic animals, the compositions may be administered by, e.g., food, or added to aquarium or tank water, and may be combined with other agents usually administered to aquatic animals, or the tank or aquarium, e.g. anti-algae agents, antimolluscides, and antihelmintics (e.g., niclosamide).

Additional Agents

The compositions, methods, and kits of the invention can further include an additional antibiotic agent selected from: aminoglycosides, such as amikacin, apramycin, arbekacin, bambermycins, butirosin, dibekacin, dihydrostreptomycin, fortimicin(s), fradiomycin, gentamicin, ispamicin, kanamycin, micronomicin, neomycin, neomycin undecylenate, netilmicin, paromomycin, ribostamycin, sisomicin, spectinomycin, streptomycin, streptonicozid, and tobramycin; amphenicols, such as azidamfenicol, chloramphenicol, chloramphenicol palmirate, chloramphenicol pantothenate, florfenicol, and thiamphenicol; ansamycins, such as rifampin, rifabutin, rifapentine, and rifaximin; β-Lactams, such as amidinocillin, amdinocillin, pivoxil, amoxicillin, ampicillin, aspoxicillin, azidocillin, azlocillin, bacampicillin, benzylpenicillinic acid, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzhydrylamine, penicillin G calcium, penicillin G hydragamine, penicillin G potassium, penicillin G, procaine, penicillin N, penicillin O, penicillin V, penicillin V benzathine, penicillin V hydrabamine, penimepicycline, phenethicillin, piperacillin, pivapicillin, propicillin, quinacillin, sulbenicillin, talampicillin, temocillin and ticarcillin; carbapenems, such as imipenem; cephalosporins, such as 1-carba (dethia) cephalosporin, cefactor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpirimide, cefpodoxime proxetil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin, cephalothin, cefaclor, cefotetan, cefprozil, loracarbef, cefetamet, and cefepime; cephamycins such as cefbuperazone, cefmetazole, cefminox, cefetan, and cefoxitin; monobactams such as aztreonam, carumonam, and tigemonan; oxacephems such as flomoxef and moxolactam; lincosamides such as clindamycin and lincomycin; macrolides such as azithromycin, carbomycin, clarithromycin, erythromycin(s) and derivatives, josamycin, leucomycins, midecamycins, miokamycin, oleandomycin, primycin, rokitamycin, rosaramicin, roxithromycin, spiramycin and troleandomycin; polypeptides such as amphomycin, bacitracin, capreomycin, colistin, enduracidin, enylomycin, fusafungine, gramicidin(s), gramicidin S, mikamycin, polymyxin, polymyxin β-methanesulfonic acid, pristinamycin, ristocetin, teicoplanin, thiostrepton, tuberactinomycin, tyrocidine, tyrothricin, vancomycin, viomycin(s), virginiamycin and zinc bacitracin; tetracyclines such as spicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin and tetracycline; and 2,4-diaminopyrimidines such as brodimoprim, tetroxoprim and trimethoprim; nitrofurans such as furaltadone, furazolium, nifuradene, nifuratel, nifurfoline, nifurpirinol, nifurprazine, nifurtoinol and nitrofurantoin; sulfonamides such as acetyl sulfamethoxypyrazine, acetyl sulfisoxazole, azosulfamide, benzylsulfamide, chloramine-β, chloramine-T, dichloramine-T, formosulfathiazole, $N_2$-formyl-sulfisomidine, $N_4$-β-D-glucosylsulfanilamide, mafenide, 4'-(methyl-sulfamoyl)sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicyclic acid, $N_4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine and sulfisoxazole; sulfones, such as acedapsone, acediasulfone, acetosulfone, dapsone, diathymosulfone, glucosulfone, solasulfone, succisulfone, sulfanilic acid, p-sulfanilylbenzylamine, p,p'-sulfonyldianiline-N,N'digalactoside, sulfoxone and thiazolsulfone; lipopeptides such as daptomycin; oxazolidones such as linezolid; ketolides such as telithromycin; and miscellaneous antibiotics such as clofoctol, hexedine, magainins, methenamine, methenamine anhydromethylene-citrate, methenamine hippurate, methenamine mandelate, methenamine sulfosalicylate, nitroxoline, squalamine, xibornol, cycloserine, mupirocin, and tuberin.

Administration

In particular embodiments of any of the methods of the invention, the two components of the combination therapy are administered within 10 days of each other, within five days of each other, within twenty-four hours of each other, or simultaneously. The compounds may be formulated together as a single composition, or may be formulated and administered separately.

Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the subject, the stage and type of the subject's disease, and how the subject responds to the treatment. Additionally, a person having a greater risk of developing a bacterial infection (e.g., a person who is undergoing a surgical procedure) may receive prophylactic treatment.

Routes of administration for the various embodiments include, but are not limited to, topical, transdermal, and systemic administration (such as, intravenous, intramuscular, subcutaneous, inhalation, rectal, buccal, vaginal, intraperitoneal, intraarticular, ophthalmic or oral administration). As used herein, "systemic administration" refers to all nondermal routes of administration, and specifically excludes topical and transdermal routes of administration.

In combination therapy, the dosage and frequency of administration of each component of the combination can be controlled independently. For example, one compound may be administered three times per day, while the second compound may be administered once per day. Combination therapy may be given in on-and-off cycles that include rest periods so that the subject's body has a chance to recover from any as yet unforeseen side effects. The compounds may also be formulated together such that one administration delivers both compounds.

Formulation

The administration of a combination of the invention (e.g., a membrane active biocide/fluoroquinolone combination) may be by any suitable means that results in an amount sufficient to treat a bacterial infection or an amount effective to reduce bacterial growth at a target site. A compound may be contained in any appropriate amount in any suitable carrier substance, and is generally present in an amount of 1-95% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Each compound of the combination may be formulated in a variety of ways that are known in the art. For example, the first and second agents may be formulated together or separately. Desirably, the first and second agents are formulated together for the simultaneous or near simultaneous administration of the agents. Such co-formulated compositions can include the two active agents (e.g., chlorhexidine and ciprofloxacin) formulated together either in a unit dosage form (e.g., in the same pill, capsule, or tablet) or non-unit dosage form (e.g., cream, liquid, or powder). It is to be understood that, when referring to the formulation of two agents in a combination therapy, the formulation technology employed is also useful for the formulation of the individual agents of the combination, as well as other combinations of the invention. By using different formulation strategies for different agents, the pharmacokinetic profiles for each agent can also be suitably matched.

Controlled Release Formulations

Administration of a combination of the invention in which one or both of the active agents is formulated for controlled release is useful where one of the agents, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; (iii) a short biological half-life; or (iv) the pharmacokinetic profile of each component must be modified to maximize the contribution of each agent, when used together, to an amount of that is therapeutically effective for treating or preventing bacterial infections. Accordingly, a sustained release formulation may be used to avoid frequent dosing that may be required in order to sustain the plasma levels of both agents at a therapeutic level. For example, in preferable oral pharmaceutical compositions of the invention, half-life and mean residency times from 10 to 20 hours for one or both agents of the combination of the invention are observed.

Many strategies can be pursued to obtain controlled release in which the rate of release outweighs the rate of metabolism of the therapeutic compound. For example, controlled release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes. The release mechanism can be controlled such that the one or both of the agents are released at period intervals, the release could be simultaneous, or a delayed release of one of the agents of the combination can be affected, when the early release of one particular agent is preferred over the other.

Controlled release formulations may include a degradable or nondegradable polymer, hydrogel, organogel, or other physical construct that modifies the bioabsorption, half-life or biodegradation of the agent. The controlled release formulation can be a material that is painted or otherwise applied onto the afflicted site, either internally or externally. In one example, the invention provides a biodegradable bolus or implant that is surgically inserted at or near a site of interest (for example, proximal to placement of a catheter). In another example, the controlled release formulation implant can be inserted into the body as part of a surgical procedure utilizing the combination to reduce the risk of infection at the site of implantation.

Kits, Packaging, and Instructions

The individually or separately formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds may vary in potency as therapy progresses); or the kit may contain multiple doses suitable for administration to multiple subjects ("bulk packaging"). The kit components may be assembled in cartons, blister packs, bottles, tubes, and the like.

The methods and compositions of the present invention can be disclosed in the form of instructions for the administration of a combination of the invention. Typically, the method is disclosed to a subject along with the sale or distribution of the compositions or kit. In some instances, instructions may be included on a label or on a package insert accompanying a pharmaceutical formulation containing a combination of the invention. The method of the present invention can be incorporated into a prepackaged therapeutic regimen designed to deliver a loading-dose regimen of a combination of the invention to a subject using the prepackaged regimen. For example, the two agents of the combination can be packaged in separate dosage units containing varying quantities of each agent along with instructions to the subject describing the timing and order in which the dosage units should be administered. Such doses may consist, for example, of one or more tablets, pills, capsules, or caplets.

Biodegradable Polymers

In particular embodiments of any of the methods, compositions, and kits of the invention, the one or both agents of the combination are incorporated as repeating units into a pharmaceutically-active biodegradable polymer.

Such biodegradable polymers can be prepared using, for example, the methods described in U.S. Pat. No. 5,798,115 and PCT Publ. No. WO2005110485, both of which are incorporated herein by reference. The biodegradable polymers of the invention optionally further include an oligomeric segment separating the agent(s) incorporated into the backbone of the polymer. By "oligomeric segment" or "Oligo" is meant a relatively short length of a repeating unit or units, generally less than about 50 monomeric units and molecular weights less than 5,000 but preferably <3,000. Preferably, Oligo is selected from polytetramethylene oxide, polycaprolactone, and mixtures thereof. The components (e.g., oligomeric segment, a first agent, and a second agent) of the biodegradable polymers of the invention can be linked directly, or via a coupling segment. By "coupling segment" is meant a molecule or chemical bond covalently linking segments together in the pharmaceutically-active polymer. Typically, coupling segments can have molecular weights ranging from 16 to 2,000 Da and have multi-functionality, but preferably di-functionality, to permit coupling of two segments. The coupling segments can be synthesized from the groups of precursor monomers selected from diols, diamines and/or a compounds containing both amine and hydroxyl groups. Precursors that can be incorporated into coupling segments include, without limitation, ethylene glycol, butane diol, hexane diol, hexamethylene diol, 1,5 pentanediol, 2,2-dimethyl-1,3 propanediol, 1,4-cyclohexane diol, 1,4-cyclohexanedimethanol, tri(ethylene glycol), poly(ethylene glycol), poly(ethylene oxide) diamine, lysine esters, silicone diols and diamines, polyether diols and diamines, carbonate diols and diamines, dihydroxy vinyl derivatives, dihydroxy diphenylsulfone, ethylene diamine, hexamethylene diamine, 1,2-diamino-2 methylpropane, 3,3-diamino-n-methyldipropylamine, 1,4 diaminobutane, 1,7 diaminoheptane, 2,2,4-trimethylhexamethylene diamine, and 1,8 diaminooctane.

Blends with Base Polymers

Where the biodegradable polymer of the invention does not have base polymer properties, it may be desirable to prepare a blend with a base polymer to produce the requisite mechanical properties, e.g., for a shaped article. Desirably, the polymer of the invention is concentrated within the nm region of the exterior polymer interface and is designed to be thermodynamically compatible with the base polymer to prevent phase separations.

Many materials having base polymer properties are known in the art. Base polymers useful in the blends of the invention can include, without limitation, polyurethane, polysulfones, polycarbonates, polysaccharides, polyesters, polyethylene, polypropylene, polystyrene, poly(acrylonitrile-butadienestyrene), polybutadiene, polyisoprene, styrenebutadiene-styrene block copolymers, styrene-isoprenestyrene block copolymers, poly-R-methylpentene, polyisobutylene, polymethyl-methacrylate, polyvinylacetate-polyacrylonitrile, polyvinyl chloride, polyethyleneterephthalate, cellulose and its esters and derivatives, polyamides, polyester-polyethers, styrene-isoprenes, styrenebutadienes, thermoplastic polyolefins, styrene-saturated olefins, polyester-polyester, ethylene-vinyl acetate ethylene-ethyl acrylate, ionomers, and thermoplastic polydienes.

Shaped Articles

Articles of the invention can be formed from a pharmaceutically-active polymer of the invention used either alone or as a blend with a base polymer. One advantage of using a polymer of the invention alone as the base polymer to form a shaped article is that because there is no polymer mixing, there is no reduction in entropy and no possibility of phase separation.

Any shaped article can be made using the compositions of the invention. For example, articles suitable for contact with bodily fluids, such as medical devices can be made using the compositions described herein. The duration of contact may be short, for example, as with surgical instruments or long term use articles such as implants. The medical devices include, without limitation, catheters, guide wires, vascular stents, micro-particles, electronic leads, probes, sensors, drug depots, transdermal patches, vascular patches, blood bags, and tubing. The medical device can be an implanted device, percutaneous device, or cutaneous device. Implanted devices include articles that are fully implanted in a patient, i.e., are completely internal. Percutaneous devices include items that penetrate the skin, thereby extending from outside the body into the body. Cutaneous devices are used superficially. Implanted devices include, without limitation, prostheses such as pacemakers, electrical leads such as pacing leads, defibrillators, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, skin, ligaments, tendons, and combination thereof. Percutaneous devices include, without limitation, catheters or various types, cannulas, drainage tubes such as chest tubes, surgical instruments such as forceps, retractors, needles, and gloves, and catheter cuffs. Cutaneous devices include, without limitation, burn dressings, wound dressings and dental hardware, such as bridge supports and bracing components.

An implantable medical device as described above is generally structured from a base metallic or polymeric platform in a solid state format. The polymer of the invention within this primary platform, either alone or as a blend, controls the release of therapeutic agents from the device.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Determination of the Minimum Inhibitory Concentration (MIC)

Broth dilution method was used to measure quantitatively the in vitro activity of an antimicrobial agent against a given bacterial isolate. First, a series of tubes/wells were prepared with a broth medium to which various concentrations of the antimicrobial agents were added. The tubes/wells were then inoculated with standardized suspension of the test organism. After overnight incubation at 35±2° C., the tests were examined and the minimum inhibitory concentration (MIC) was determined. The procedures were performed under aseptic conditions.

Stock culture: Stock cultures were maintained in Mueller Hinton Broth containing 15% Glycerol and stored at −80° C. Stock cultures were sub-cultured on to Mueller Hinton Agar (MHA), and incubated overnight at 37° C.

Preparation of inoculum: a single isolated colony of the same morphologic type from the MH agar plate culture was selected, inoculated into a sterile tube containing 25 mL of MH broth, and incubated at 37° C. overnight in a shaking incubator.

Washing of cells: the cells were washed with PBS (pH 7.1) by centrifuging at 3000 rpm for 10 minutes. A cell suspension in Mueller Hinton broth (MHB) having a turbidity equivalent to a 0.5 McFarland turbidity standard was prepared using a Beckman Coulter DU 800 Spectrophotometer measuring at 600 nm wavelength. This is a suspension containing approximately $\times 10^8$ CFU/mL of microbe. The suspension was diluted in MH broth so that, after dilution, the tube contained approximately $5 \times 10^6$ CFU/mL, and after inoculation, each well contains approximately $5 \times 10^5$ CFU/mL.

Broth dilution procedure: small volumes of MH broth dispensed in sterile, polystyrene, non-pyrogenic tissue culture plates, 96 well, flat bottoms with low evaporation lid were prepared (each well contained 0.1 mL of MH broth) followed by the final two fold dilutions of antimicrobial agent dispensed volumetrically into the broth. The MIC was determined using concentrations derived from serial twofold dilutions indexed to the base 2 (e.g., 1, 2, 4, 8, 16 ug/mL ... etc.).

Inoculation: each well of a microdilution plate was inoculated. The purity of the inoculum suspension was checked by sub-culturing an aliquot on to MH agar plate. Colony counts on inoculum suspensions were performed periodically, to ensure that the final inoculum concentration was approximately $5 \times 10^6$ CFU/mL. Both a positive (0.1 mL of MH broth with 10 μL of inoculum) and a negative (0.1 mL of MH Broth only) control were performed with each microtitre plate. To prevent drying, each plate was sealed with parafilm and the plates were kept in a moist chamber while incubating at 37° C. overnight, in a shaking incubator.

Determining MIC endpoints: The MIC is defined as the lowest concentration of an antimicrobial that will inhibit growth of a microorganism. The in plate dilution method the endpoint is detected by the unaided eye. If, for example, in a two fold dilution scheme-if one detects growth at 2 μg/mL, the MIC is reported between 4 and 2 μg/mL. The results are summarized in Table 1 and Table 2 below.

TABLE 1

MIC Data

| Agent(s) | MIC (μg/mL) Microorganism | | |
|---|---|---|---|
| | E. coli | P. Auregenosa | S. Aureus |
| Monotherapy | | | |
| Ciprofloxacin | 0.005-0.0078 | 0.156-0.25 | 0.156-0.2 |
| Polymixin B | 7.8-10 | 3.125-5.0 | 62.5-100.0 |
| Chlorhexidine | 3.13-4.0 | 4.0-5.0 | 3.125-4.0 |
| Bacitracin | 1000-1250 | 4000-5000 | 35-40 |
| Aztreonam | 0.078-0.097 | 15.62-19.0 | 625-1250 |
| Gentamicin | 1.25-2.5 | 0.625-1.25 | N.D. |
| Vancomycin | 190.0-380.0 | N.D. | N.D. |
| Amoxicillin | N.D. | 250-500 | 31.25-62.5 |
| Sulfamethoxazole | N.D. | N.D. | 64 0-70.0 |
| Miconazole | N.D. | N.D. | 45.0-90.0 |
| Combination Therapy[c] | | | |
| Ciprofloxacin/Bacitracin | N.I. | 0.078-0.125[a] | N.I. |
| Bacitracin/Ciprofloxacin/ | N.I. | 625-1250 | N.I. |
| Ciprofloxacin/Chlorhexidine | 0.0025-0.0039[a] | N.I. | N.I. |
| Chlorhexidine/Ciprofloxacin | 0.125-0.195 | N.I. | N.I. |
| Ciprofloxacin/Polymixin B | 0.0025-0.0039[a] | N.I. | N.I. |
| Polymixin B/Ciprofloxacin | 1.25-1.95 | N.I. | N.I. |

TABLE 1-continued

MIC Data

| Agent(s) | MIC (μg/mL) Microorganism | | |
|---|---|---|---|
| | E. coli | P. Auregenosa | S. Aureus |
| Aztreonam/Chlorhexidine | N.I. | 0.625-0.78[b] | N.I. |
| Chlorhexidine/Aztreonam | N.I. | 7.8-9.76 | N.I. |
| Polymixin B/Gentamicin | 3.9-5.0[c] | 2.5-3.125[c] | N.I. |
| Gentamicin/Polymixin B | 0.25-0.3125 | 0.15-0.25 | N.I. |
| Polymixin B/Aztreonam | 2.5-3.125[d] | N.I. | N.I. |
| Aztreonam/Polymixin B | 0.024-0.039 | N.I. | N.I. |
| Polymixin B/Vancomycin | N.I. | 1.56-2.5[e] | N.I. |
| Vancomycin/Polymixin B | N.I. | 16.0-25.0 | N.I. |
| Bacitracin/Aztreonam | N.I. | 2000-2500[f] | 17.5-20[f] |
| Aztreonam/Bacitracin | N.I. | 2.44-4.88 | 78.1-156.2 |
| Polymixin B/Amoxicillin | N.I. | 0.975-1.25[g] | N.I. |
| Amoxicillin/Polymixin B | N.I. | 64.0-128.0 | N.I. |
| Bacitracin/Amoxicillin | N.I. | 1000-2000[h] | N.I. |
| Amoxicillin/Bacitracin | N.I. | 62.5-125.0 | N.I. |
| Polymixin B/Miconazole | N.I. | N.I. | 7.8-15.6[i] |
| Miconazole/Polymixin B | N.I. | N.I. | 11.25-22.5 |
| Bacitracin/Miconazole | N.I. | N.I. | 10.0-12.5[i] |
| Miconazole/Bacitracin | N.I. | N.I. | 5.6-11.25 |
| Miconazole/Sulfa | N.I. | N.I. | 11.25-22.5[i] |
| Sulfa/Miconazole | N.I. | N.I. | 16.0-25.0 |
| Amoxicillin/Sulfa | N.I. | N.I. | 7.8-15.6[j] |
| Sulfa/Amoxicillin | N.I. | N.I. | 16.0-25.0 |

N.D. = no data.
N.I. = no improvement over the monotherapy MIC data was observed.
a = Sulfamethoxazole
[a]The MIC of ciprofloxacin is reduced in the presence of a membrane active biocide.
[b]The MIC of aztreonam is reduced in the presence of chlorhexidine.
[c]The MIC of gentamicin is reduced in the presence of a membrane active biocide
[d]The MIC of aztreonam is reduced in the presence of polymixin B.
[e]The MIC of vancomycin is reduced in the presence of a second membrane active biocide in a gram negative organism (Note: Vancomycin not active against gram negative bacteria.)
[f]The MIC of aztreonam is reduced in the presence of aztreonam.
[g]The MIC of amoxicillin is reduced in the presence of polymixin B.
[h]The MIC of amoxicillin is reduced in the presence of bacitracin.
[i]The MIC of miconazole is reduced in the presence of a membrane active biocide.
[j]The MIC of sulfamethoxazole is reduced in the presence of a membrane active biocide.
[k]The data reported for each combination therapy refers to the MIC in μg/mL of the first agent listed (i.e., ciprofloxacin or aztreonam). The second agent of the combination therapy is present at a concentration some number of dilutions below the lower MIC limit observed for the use of the second agent as a monotherapy (i.e., for chlorhexidine the concentration is less than 3.13 μg/mL). Thus, the second agent is present in an amount at which no inhibition of microbial growth should be observed when used as a monotherapy.

TABLE 2

MIC Data

| Agent(s) | MIC (μg/mL) Microorganism C. Albicans |
|---|---|
| Monotherapy | |
| Ciprofloxacin | >2.5 |
| Chlorhexidine | 3.125-4.0 |
| Miconazole | 1.4-2.8 |
| Combination Therapy[c] | |
| Ciprofloxacin/Chlorhexidine | 0.312-0.625[a] |
| Chlorhexidine/Ciprofloxacin | 1.56-3.125 |
| Ciprofloxacin/Miconazole | 0.125-0.155[a] |
| Miconazole/Ciprofloxacin | 07-1.4 |

[a]The MIC of ciprofloxacin is reduced in the presence of a membrane active biocide.
[b]The data reported for each combination therapy refers to the MIC in μg/mL of the first agent listed. The second agent of the combination therapy is present at a concentration some number of dilutions below the lower MIC limit observed for the use of the second agent as a monotherapy (i.e., for chlorhexidine the concentration is less than 3.13 μg/mL). Thus, the second agent is present in an amount at which no inhibition of microbial growth should be observed when used as a monotherapy.

The results provided in Tables 1 and 2 show that the combinations of the invention can work together synergistically to produce a composition having superior and unexpected antibacterial and antifungal properties in comparison to the use of the individual components alone.

EXAMPLE 2

General Synthesis of Bioactive Monomers Containing a Membrane Active Biocide or a Fluoroquinolone A protocol for the general synthesis of a biological coupling agents (e.g., a membrane active biocide-containing monomeric unit or a fluoroquinolone-containing monomeric unit) is set forth below in steps A-D and Scheme A.

Step A:

To a dry 2 L round bottom flask flushed with nitrogen was added ciprofloxacin hydrochloride (100 g, 301.8 mmol), trityl chloride (185.1 g, 663.9 mmol) and chloroform (1000 mL). To this stirring suspension triethylamine (135 mL, 965.8 mmol) was added dropwise and the resulting mixture was stirred at room temperature for 4 h, during which time a homogeneous yellow solution resulted. The resulting solution was treated with methanol (500 mL) and stirred at 50° C. for 1.5 h. The resulting solution was washed with water (2×2 L). The organic layer was dried over sodium sulphate, filtered, and solvent removed under reduced pressure until precipitate first begins to form. A couple of drops of methanol was added and flask placed in refrigerator overnight. The product was collected by filtration (160 g, 90%).

Step B:

To a dry 2 L round bottom flask flushed with nitrogen was added 1 ((50 g, 87.16 mmol) and dichloromethane (900 mL). Reagent 1 was allowed to dissolve before the addition of tri(ethyleneglycol) (6.23 g, 41.45 mmol) and dimethylaminopyridine (5.33 g, 43.59 mmol). The resulting solution was cooled to 0° C. before the addition of EDAC-HCl (66.75 g, 348.2 mmol) and the reaction was allowed to continue overnight with warming then for a week at room temperature. The progress of the reaction is monitored by TLC. Upon complete consumption of 1 as detected by TLC the solvent is removed.

The product is recovered by recrystallization with chloroform methanol. This produces 37.63 g (68%) of the desired product, C.

Step C:

To a dry 1 L round bottom flask was added 2 (100 g, 79.27 mmol) and dichloromethane (344 mL). To this stirring solution was added trifluoroacetic (24 mL), and water (12 mL). The reaction was stirred at room temperature for 5 hours. The progress of the reaction was monitored by TLC. During the course of the reaction the desired STEP D: product precipitated from the reaction. The product was isolated by filtration and washed with chloroform (2×100 mL). This produced 78.42 g (98%) of the desired product.

Step D:

To a dry 1 L round bottom flask was added 3 (100 g, 99.52 mmol), water (150 mL) and chloroform (200 mL). To this heterogeneous white mixture at room temperature was slowly added a saturated aqueous solution of sodium bicarbonate. The reaction mixture effervesced upon each addition of base. The progress of the reaction was followed by pH. The addition of bicarbonate solution was done until the pH of the solution was approximately 8. Filtration of the white solid followed by washing with water (150 mL), and drying overnight under vacuum produced the desired product. This produced 78.42 g (98%) of the compound 4.

$^1$H NMR of CIPRO-TEG-CIPRO: (400 MHz, DMSO). δ: 9.16 (bs, 2H, NH—R), 8.30 (s, 2H, H$^2$, ar), 7.49 (d, 2H, J=13.2 Hz, H$^5$, ar), 7.34 (d, 2H, J=7.6 Hz, H$^8$, ar), 4.25 (t, 4H, J=5.2 Hz, N—CH(CH$_2$)$_2$); 3.73 (t, 4H, J=4.4 Hz, CO$_2$CH$_2$), 3.46-3.30 (m, 16H, piperazine), 1.22 (q, 4H, J=6.4 Hz, CH(CH$_2$ CH$_2$)), 1.07 (m, 4H, CH(CH$_2$CH$_2$)).

$^{13}$C NMR of CIPRO-TEG-CIPRO: (400 MHz, DMSO). δ: 171.9, 164.1, 158.7, 153.9, 151.5, 148.4, 143.0, 142.9, 138.1, 122.6, 122.5, 111.9, 111.7, 109.2, 107.0, 79.6, 70.5, 70.4, 68.9, 63.7, 47.0, 43.2, 35.3, 7.9.

ES-MS of CIPRO-TEG-CIPRO (m/z, %) (Positive mode): Calculated for mass C$_{40}$H$_{46}$F$_2$N$_6$O$_8$: 776 amu; found 777 (M+H$^+$); 389 (M+2H)$^+$.

Scheme A: Synthetic route for Bioactive Monomer

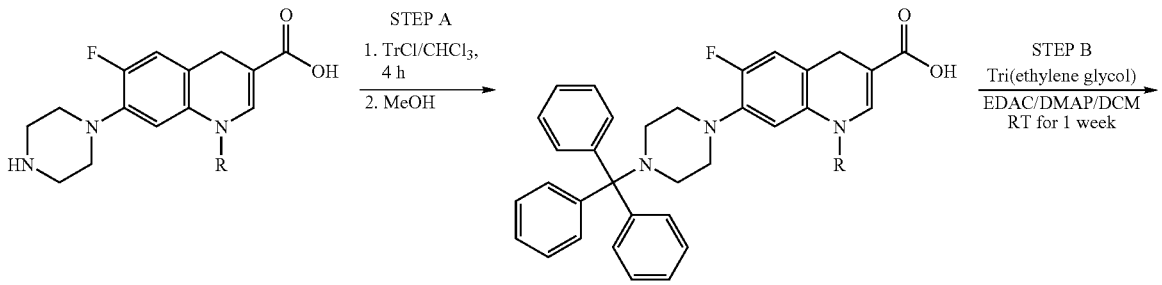

1

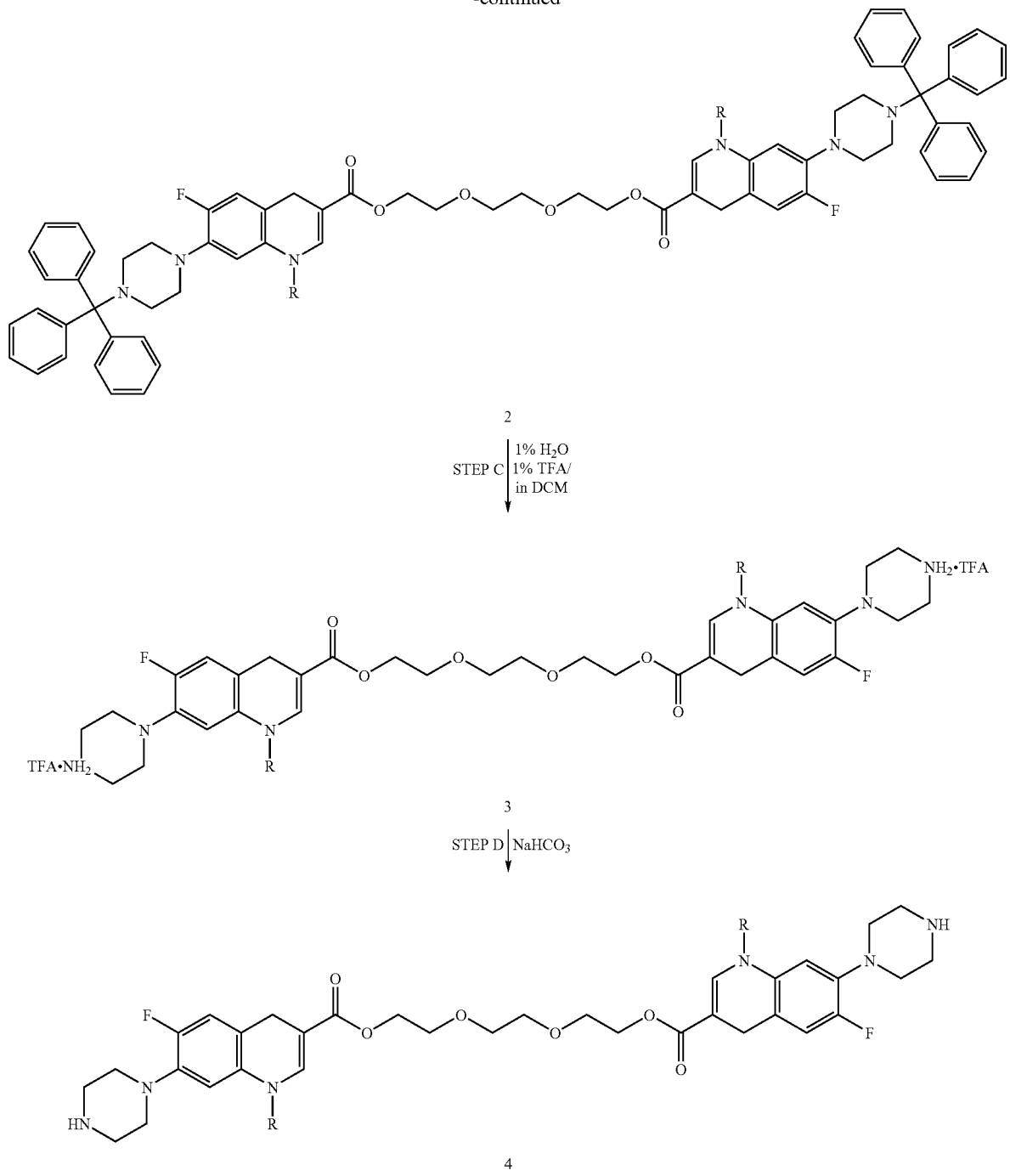

EXAMPLE 3

Synthesis of Ciprofloxacin Polymer

To a dry 1 L round bottom flask flushed with nitrogen was added polycaprolactone diol (200 g, 100 mmol). The flask was heated to 70° C. for 2 hours under vacuum. The temperature was decreased to 65° C. before the addition of DMSO (100 mL), dibutyltin dilaureate (3.2 mL, 5.0 mmol) and THDI (32 mL, 155 mmol). The reaction mixture was stirred for 1 h at 65° C. before the addition of 4 (38.84 g, 50 mmol) solution in DMSO (500 mL) and dibutyltin dilaureate (1.8 mL, 3.0 mmol). The reaction was continued to stir for 17 h at 65° C. under inert atmosphere. The reaction was quenched with the addition of methanol (78 mL) and left to stir for an addition 1 hour. The polymer was transferred to a dropping funnel where it was added dropwise to hexane (2 L). Upon discarding the supernatant, the polymer was taken up in isopropanol and again added dropwise to hexane (2 L). The process was repeated with water as the precipitant. The resulting polymer mass is dissolved in isopropanol. To this solution was added EDTA ammonium salt solution (described below) dropwise. The polymer was taken up in isopropanol and washed with water (1×1 L) and finally washed with hexane (2×1 L).

EXAMPLE 4

Synthesis of Chlorhexidine Polymer

To a dry 1 L round bottom flask flushed with nitrogen was added polycaprolactone diol (150 g, 75 mmol). The flask was heated to 70° C. for 2 hours under vacuum. The temperature was decreased to 65° C. before the addition of DMSO (400 mL), dibutyltin dilaureate (4.4 mL, 7.5 mmol) and THDI (24 mL, 116.25 mmol). The reaction mixture was stirred for 4 h at 65° C. before the addition of chlorhexidine (18.96 g, 37.5 mmol) solution in DMSO (100 mL) and dibutyltin dilaureate (2.7 mL, 4.5 mmol). The reaction was continued to stir for 17 h at 65° C. under inert atmosphere. The reaction was quenched with the addition of methanol (100 mL) and left to stir for an addition 1 hour. The polymer was transferred to a dropping funnel where it was added dropwise to hexane (2 L). Upon discarding the supernatant, the polymer was taken up in isopropanol and again added dropwise to hexane (2 L). The process was repeated with water as the precipitant. The resulting polymer mass is dissolved in isopropanol. To this solution is added EDTA ammonium salt solution (described below) dropwise. The polymer is taken up in isopropanol and washed with water (1×1 L) and finally washed with hexane (2×1 L).

EXAMPLE 5

Article Coated with Ciprofloxacin Polymer and Chlorhexidine Polymer

The ciprofloxacin polymer and chlorhexidine polymer described in examples 3 and 4 can be used in the methods and kits of the invention. For example, the polymers can be used to coat a catheter cuff and thereby reduce the risk of infection by locally releasing a membrane active biocide and fluoroquinolone in vivo following implantation of the catheter in a subject.

OTHER EMBODIMENTS

All publications, patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

What we claim is:

1. A shaped article comprising a composition wherein
   said composition comprises a combination of a membrane active biocide that is a cationic biguanide antibacterial agent and a second agent selected from fluoroquinolones;
   wherein said composition comprises a biodegradable polymer having a first repeating unit and a second repeating unit, said first repeating unit comprising a membrane active biocide that is a cationic biguanide antibacterial agent and said second repeating unit comprising an agent that is a fluoroquinolone, and
   wherein said shaped article is in the form of an implantable medical device.

2. The shaped article of claim 1, wherein said implantable medical device is a cardiac-assist device, a catheter, a stent, a prosthetic implant, a suture, a cuff, a mesh, a hernia patch, a wound dressing, a bandage, an artificial sphincter, or a drug delivery device.

3. The shaped article of claim 1, wherein said membrane active biocide is chlorhexidine and said second agent is ciprofloxacin.

4. The shaped article of claim 2, wherein said membrane active biocide is chlorhexidine and said second agent is ciprofloxacin.

5. The shaped article of claim 1, wherein said membrane active biocide is chlorhexidine.

6. The shaped article of claim 1, wherein said second agent is a fluoroquinolone selected from ciprofloxacin, enrofloxacin, enoxacin, gatifloxacin, gemifloxacin, levofloxacin, lomefloxacin, moxifloxacin, norfloxacin, ofloxacin, sparfloxacin, trovafloxacin, difloxacin, cinofloxacin, pefloxacin, tosufloxacin, temafloxacin, fleroxacin, amifloxacin, binfloxacin, danofloxacin, marbofloxacin, ruflocaxin, and sarafloxacin.

* * * * *

UNITED STATES PATENT AND TRADEMARK OFFICE
CERTIFICATE OF CORRECTION

| | |
|---|---|
| PATENT NO. | : 8,357,385 B2 |
| APPLICATION NO. | : 12/419733 |
| DATED | : January 22, 2013 |
| INVENTOR(S) | : Frank Laronde, Hanje Chen and Selva Sinnadurai |

It is certified that error appears in the above-identified patent and that said Letters Patent is hereby corrected as shown below:

On the Title Page, Item (56), Other Publications, Martin-Navarro et al., replace "chlorhexidine-sensittive" with --chlorhexidine-sensitive--.

In the Specification

Column 9, Line 30, replace "EPO47005" with --EP047005--.

Column 19, Line 37, replace "two fold" with --two-fold--.

Column 20, Line 31, replace "a=Sulfamethoxazole" with --"Sulfa=Sulfamethoxazole"--.

In the Claims

Column 26, Line 42, replace "ruflocaxin" with --rufloxacin--.

Signed and Sealed this
Sixteenth Day of December, 2014

Michelle K. Lee
*Deputy Director of the United States Patent and Trademark Office*